US006280972B1

(12) United States Patent
Yasueda

(10) Patent No.: US 6,280,972 B1
(45) Date of Patent: Aug. 28, 2001

(54) ACTIVATOR FOR METHANOL DEHYDROGENASE AND GENE THEREOF

(75) Inventor: Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/387,800

(22) Filed: Sep. 1, 1999

(30) Foreign Application Priority Data

Sep. 2, 1998 (JP) .................................................. 10-248297

(51) Int. Cl.[7] .............................. C12P 21/06; C12Q 1/68; C12N 15/09; C07K 1/00; C07H 21/04
(52) U.S. Cl. .......................... 435/69.1; 435/6; 435/320.1; 536/23.1; 530/350
(58) Field of Search ................................. 536/23.1, 23.2; 435/320.1, 69.1, 6; 530/350

(56) References Cited

PUBLICATIONS

Amann, E. et al., Gene, vol. 69, pp. 301–315, 1988.*
Kobayashi, Y. et al., GenBank Database, Accession No. P54570, Oct. 1, 1996.*
Kunst, F. et al., GenBank Database, Accession No. 2634723, Nov. 26, 1997.*
Naeve, et al., BioTechniques, vol. 19, No. 3, pp. 448–453, 1995.*
Nico Arfman, et al., The Journal of Biological Chemistry, vol. 266, No. 6, pp. 3955–3960, "Purification and Characterization of an Activator Protein for Methanol Dehydrogenase from Thermotolerant Bacillus Spp", Feb. 25, 1991.
Nico Arfman, et al., Eur. J. Biochem., vol. 244, pp. 426–433, "Properties of an NAD (H)–Containing Methanol Dehydrogenase and Its Activator Protein from *Bacillus Methanolicus*", 1997.

* cited by examiner

*Primary Examiner*—Ponnathapu Achutamurthy
*Assistant Examiner*—Peter P. Tung
(74) *Attorney, Agent, or Firm*—Oblon, Spivak, McClelland, Maier & Neustadt, P.C.

(57) ABSTRACT

A cell which is introduced with a DNA coding for a protein defined in the following (A) or (B):

(A) a protein which has the amino acid sequence of SEQ ID NO: 2 shown in Sequence Listing;

(B) a protein which has the amino acid sequence of SEQ ID NO: 2 shown in Sequence Listing including substitution, deletion, insertion, addition, or inversion of one or several amino acids, and has activity to promote methanol dehydrogenase activity, in such a manner that the protein encoded by the DNA can be expressed, is cultured in a medium so that the protein having an activity to promote methanol dehydrogenase activity should be produced and accumulated in the medium, and the protein is collected from the medium. The present invention provides a novel activator of methanol dehydrogenase, DNA coding for it, cell expressing the DNA, and method for producing the activator.

3 Claims, No Drawings

ACTIVATOR FOR METHANOL DEHYDROGENASE AND GENE THEREOF

TECHNICAL FIELD

The present invention relates to a novel activator of methanol dehydrogenase, DNA coding for it, cell expressing the DNA, and method for producing the activator.

BACKGROUND ART

The *Bacillus methanolicus* strain C1, which is a methanol assimilating bacterium belonging to the genus Bacillus, has been known to have methanol dehydrogenase (also referred to with an abbreviation "MDH" hereinafter), which oxidizes methanol used as a carbon source into formaldehyde (*Arch. Microbiol.*, 152, 280–288, 1989). MDH may be used for measurement of methanol content in a sample. In such a purpose, it is important to increase the specific activity of the enzyme, and means for achieving it have long been desired.

Arfman et al. has recently reported that a factor promoting this enzyme activity of MDH is contained in the *Bacillus methanolicus* C1. They purified a protein constituting the factor, and determined a partial amino acid sequence of the N-terminus of this protein (*The Journal of Biological Chemistry*, 266, 3955–3960, 1991). However, neither the whole structure of this factor and nor the genetic structure therefor has not been known at all.

By the way, *Bacillus subtilis* could not grow by utilizing methanol as an only carbon source, and therefore it has not been thought at all that this microorganism has methanol dehydrogenase, which is used for the first reaction of the methanol assimilation. In fact, when the present inventors searched known chromosome DNA sequences of *Bacillus subtilis* for a gene product or gene which has significant homology with the amino acid sequence and the nucleotide sequence of MDH of the *Bacillus methanolicus* C1, such a gene product or gene has not been found. Therefore, in microorganism not assimilating methanol like *Bacillus subtilis*, any activator of MDH has not been known, and its existence has not been expected.

SUMMARY OF THE INVENTION

The object of the present invention is to provide a novel means for promoting the MDH activity.

While the present inventors studied various gene sequences on the genome of *Bacillus subtilis* which is not a methanol assimilating bacterium, they accidentally found that the bacterium had a gene which could code for a protein homologous to the methanol dehydrogenase activator (MDH activator). When this gene was forcibly expressed in *Escherichia coli*, activity that promoted methanol dehydrogenase activity was successfully detected. Thus, the present invention has been accomplished.

That is, the present invention relates to a protein defined in the following (A) or (B):

(A) a protein which has an amino acid sequence of SEQ ID NO: 2;

(B) a protein which has an amino acid sequence of SEQ ID NO: 2 including substitution, deletion, insertion, addition, or inversion of one or several amino acids, and has an activity to promote methanol dehydrogenase activity.

The present invention also provides a DNA which codes for a protein defined in the following (A) or (B):

(A) a protein which has an amino acid sequence of SEQ ID NO: 2;

(B) a protein which has an amino acid sequence of SEQ ID NO: 2 including substitution, deletion, insertion, addition, or inversion of one or several amino acids, and has an activity to promote methanol dehydrogenase activity.

Specific examples of the above DNA include a DNA defined in the following (a) or (b):

(a) a DNA which comprises a nucleotide sequence of SEQ ID NO: 1;

(b) a DNA which is hybridizable with a nucleotide sequence of SEQ ID NO: 1 or a probe prepared from the nucleotide sequence under a stringent condition, and codes for a protein having an activity to promote methanol dehydrogenase activity.

The above stringent condition is exemplified by the condition in which in which washing is performed at 60 C, and at a salt concentration corresponding to 1×SSC and 0.1% SDS The present invention also provides a cell to which the aforementioned DNA is introduced in such a manner that a protein encoded by the DNA can be expressed.

The present invention further provides a method for producing a protein having an activity to promote methanol dehydrogenase activity, which comprises culturing the aforementioned cell in a medium to produce and accumulate the protein, and collecting the protein.

For the purpose of the present invention, "methanol dehydrogenase activity" means an activity catalyzing the reaction in which methanol is oxidized to generate formaldehyde. The "activity to promote methanol dehydrogenase activity" means an activity that significantly increases specific activity of methanol dehydrogenase, when a factor which has this activity coexists with the methanol dehydrogenase.

A protein which has the activity to promote the methanol dehydrogenase activity according to the present invention will be referred to as "MDH activator" hereinafter.

According to the present invention, there is provided a novel activator for methanol dehydrogenase. This MDH activator can be utilized for basic researches for the reaction mechanism analysis of methanol dehydrogenase as well as industrially important processes such as detection of alcohol concentration in objective samples. Moreover, according to the present invention, DNA that encodes the alcohol dehydrogenase activator is obtained, and it enables efficient production of the factor. Therefore, this factor can be provided in a large scale at a low cost.

DETAILED DESCRIPTION OF THE INVENTION

Hereafter, the present invention will be explained in detail.

The DNA of the present invention can be obtained through PCR (polymerase chain reaction) utilizing chromosome DNA of *Bacillus subtilis*, for example, the *Bacillus subtilis* strain 168, as a template, as well as a primer having the nucleotide sequence of SEQ ID NO: 5 shown in Sequence Listing (BsYqk-G1) and a primer having the nucleotide sequence of SEQ ID NO: 6 shown in Sequence Listing (BsYqk-G2). Because both of these primers have restriction enzyme ClaI or BamHI recognition sites in their 5' sequences, the amplification product digested with these restriction enzymes can be inserted into a vector having ClaI and BamHI digested ends.

The nucleotide sequences of the aforementioned primers were designed based on the nucleotide sequence of yqkG gene (SEQ ID NO: 2), of which function is unknown, and the amino acid sequence of the gene product thereof (SEQ ID NO: 1) of a *Bacillus subtilis*, which had been found as one of the genes having an amino acid sequence highly homologous to that of the MDH activator derived from methanol assimilating *Bacillus methanolicus* strain C1 through database searching based on partial amino acid sequence information of that sequence (SEQ ID NO: 7). By using these primers, a DNA fragment containing the coding region of the yqkg gene and its flanking region (3' non-translation region of about 390 bases) can be obtained.

The nucleotide sequence of the coding region of the DNA of the present invention obtained as described above and an amino acid sequence which may be encoded by the sequence are shown in SEQ ID NO: 1. The amino acid sequence alone is shown in SEQ ID NO: 2. These sequences were identical to the known sequences of yqkg.

At first, it was scarcely expected that *Bacillus subtilis* not assimilating methanol retained on a genome a gene for an enzyme which participated in the methanol assimilation and metabolism like the MDH activator, and, moreover, it had evolved up to now while retaining the gene in such a form that it can express an active enzyme therefrom. This is because it is generally considered that, even if such a gene of enzyme that had become unnecessary for the growth of *Bacillus subtilis* is retained, it had suffered random mutations during the evolution of the microorganism, and lost its activity.

However, the present inventors dared to clone the open reading frame (also abbreviated as ORF hereinafter), and expressed it in a forced expression system utilizing *Escherichia coli* as a host in order to confirm whether the yqkG gene, of which function is unknown, actually codes for an alcohol dehydrogenase activator which can actually enhance the enzyme activity. As a result, the expression product showed the activity to promote the MDH activity as will be described in the examples hereinafter. The DNA coding the MDH activator of the present invention was designated as and (Activator of Methanol Dehydrogenase).

While the DNA of the present invention was obtained by PCR as described above, it can also be obtained from a chromosome DNA library of *Bacillus subtilis* by hybridization utilizing a probe composed of an oligonucleotide prepared based on the nucleotide sequence of the DNA of the present invention.

Methods for construction of genomic DNA library, hybridization, PCR, preparation of plasmid DNA, digestion and ligation of DNA, transformation and the like are described in Sambrook, J., Fritsch, and E. F., Maniatis, T., Molecular Cloning, Cold Spring Harbor Laboratory Press, 1.21 (1989).

The DNA of the present invention may code for MDH activator including substitution, deletion, insertion, addition, or inversion of one or several amino acids at one or a plurality of positions, provided that the activity to enhance MDH activity of MDH activator encoded thereby is not deteriorated. Although the number of "several" amino acids differs depending on the position or the type of amino acid residues in the three-dimensional structure of the protein, it may be 2 to 100, preferably 2 to 50, and more preferably 2 to 10.

DNA, which codes for the substantially same protein as MDH activator as described above, is obtained, for example, by modifying the nucleotide sequence of MDH activator gene, for example, by means of the site-directed mutagenesis method so that one or more amino acid residues at a specified site of the gene involve substitution, deletion, insertion, addition, or inversion. DNA modified as described above may be obtained by the conventionally known mutation treatment. The mutation treatment includes a method for treating DNA coding for MDH activator in vitro, for example, with hydroxylamine, and a method for treating a microorganism, for example, a bacterium belonging to the genus Escherichia harboring DNA coding for MDH activator with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutation (mutant or variant) which naturally occurs, for example, the difference in strains, species or genera of the microorganism.

The DNA, which codes for substantially the same protein as MDH activator, is obtained by expressing DNA having mutation as described above in an appropriate cell, and investigating the activity to enhance MDH of an expressed product. The DNA, which codes for substantially the same protein as MDH activator, is also obtained by isolating DNA which is hybridizable with DNA having, for example, the nucleotide sequence of SEQ ID NO: 1 or a probe which can be prepared from the DNA, under a stringent condition, and which codes for a protein having the activity to enhance MDH, from DNA coding for MDH activator having mutation or from a cell harboring it. The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 50% are hybridized with each other, and DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 60° C., 1×SSC, 0.1% SDS, preferably 0.1×SSC, 0.1% SDS.

The gene, which is hybridizable under the condition as described above, includes those having a stop codon generated in the gene, and those having no activity due to mutation of active center. However, such mutant genes can be easily removed by ligating the gene with a commercially available activity expression vector, and measuring the activity to enhance MDH in accordance with the method described below.

The MDH activator can be produced by expressing the DNA (and gene) coding for the MDH activator of the present invention using a suitable host-vector system.

As a host for the expression of the and gene, various prokaryotic cells including bacteria belonging to the genera Escherichia, Bacillus, Brevibacterium and Corynebacterium such as *Escherichia coli, Bacillus subtilis, Bacillus brevis Bacillus methanolicus*, methanol assimilating bacteria belonging to the genera Methylophilus, Methylobacillus and Methylobacterium, various eukaryotic cells including *Saccharomyces cerevisiae*, animal cells, and plant cells can be mentioned. Among these, prokaryotic cells, in particular, *Escherichia coli* and *Bacillus subtilis* are preferred. While *Bacillus subtilis* inherently retains the amd gene, forced expression of the amd gene enables accumulation of the MDH activator in it.

As the vector for introducing the amd gene into the aforementioned host, for example, pUC19, pUC18, pBR322, pHSG299, pHSG298, pHSG399, pHSG398, RSF1010, pMW119, pMW118, pMW219, pMW218, IncQ type plasmid such as RSF1010, IncP type plasmid such as pRK310, IncW type plasmid such as pSa, pBBR1 (Molecular Microbiology, 1992, vol.6(13), 1785–1799), pAM330 (Japanese Patent Laid-open No. 58-67699) and the like can be mentioned. Phage vector DNA can also be utilized. The amd gene can be introduced into a host by transforming the host with a recombinant DNA vector obtained by ligating the and gene to any of these vectors. The amd gene can also be incorporated into chromosome of the host by a method utilizing transduction, transposon (Berg, D. E. and Berg, C. M., Bio/Technol., 1,417 (1983)), Mu phage (Japanese Patent Unexamined Publication [EKOKAI] No. 2-109985), or homologous recombination (Experiments in Molecular Genetics, Cold Spring Harbor Lab. (1972)).

Further, in order to obtain efficient expression of the amd gene, a promoter functioning in the host cell such as lac, trp, $P_L$, tet and tac may be ligated at the upstream of the DNA sequence coding for the MDH activator. By utilizing a vector containing a promoter as the vector, the ligation of the amd gene to vector and promoter can be performed by one step. As such a vector, pT13sNco containing trp promoter (described in J. Biochem. 104, 30–34, 1988) can be mentioned.

The transformation can be attained by, for example, the method in which recipient cells are treated with calcium chloride to increase permeability for DNA as reported for Escherichia coli K-12 strain (Mandel, M. and Higa, A., J. Mol. Biol., 53, 159 (1970)), or the method utilizing introduction of DNA into competent cells produced from cells at a growth phase as reported for Bacillus subtilis (Duncan, C. H., Wilson, G. A., and Young, F. E., Gene, 1, 153 (1977)). It is also possible to prepare a protoplast or spheroplast of DNA recipient cell, which readily incorporates DNA, and introduce DNA into it as known for Bacillus subtilis, Actinomycetes and yeast (Changs, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B., and Fink, G. R., Proc. Natl. Acad. Sci. USA, 75, 1929 (1978)). Further, transformation may be performed by electroporation. The method can be suitably selected from these depending on the cell to be used as the host.

The MDH activator can be produced by culturing cells introduced with the and gene as described above in a medium so that the MDH activator should be formed and accumulated in the culture, and collecting the MDH activator from the culture. The medium used for the culture can be suitably selected depending on the host to be used. When the MDH activator is expressed with trp promoter using Escherichia coli as a host, M9-casamino acid-glucose medium is preferred. When the culture is performed at 37° C., indoleacrylic acid (IAA), which is an inducer of the trp promoter, is added to the medium to a final concentration of 25 µg/ml several hours after starting the culture, and the culture is further continued, the MDH activator will accumulate it the cells. When the MDH activator is produced so that it should be extracellularly secreted utilizing a suitable secretion system, the MDH activator accumulates in the medium.

The MDH activator produced as described above can be purified from a cell extract or medium as required by using a usual purification method for enzymes, for example, ion exchange chromatography, gel filtration chromatography, adsorption chromatography, solvent recipitation and the like.

By adding the MDH activator of the present invention to an MDH reaction mixture, the specific activity of MDH can be increased. Therefore, it can be used, for example, when content of methanol in a sample is measured by using MDH. While the target enzyme whose activity is enhanced by the MDH activator of the present invention is not particularly limited so long as it is MDH, examples thereof include MDHs produced by Bacillus brevis, Bacillus methanolicus, Brevibacterium methylicum and the like. Although the amount of the MDH activator added to an MDH reaction mixture is not particularly limited, for example, such an amount that the molecular number ratio of MDH and MDH activator should be 2:1 to 1:5 may be considered a standard of the amount used.

MDH of Bacillus brevis can be obtained by expressing a gene coding for the MHD (mdh) in Escherichia coli. The mdh gene of Bacillus brevis can be obtained through PCR (polymerase chain reaction) using chromosome DNA of Bacillus brevis, for example, Bacillus brevis strain S1, as a template, and a primer having the nucleotide sequence of SEQ ID NO: 3 shown in Sequence Listing (MDH-BM-1) and a primer having the nucleotide sequence of SEQ ID NO: 4 shown in Sequence Listing (MDH-BM-2).

The MDH activity can be determined by estimating reduction of $NAD^+$ (nicotinamide adenine dinucleotide) accompanying the oxidation of methanol into formaldehyde through measurement of absorbance for light at a wavelength of 340 nm, as shown in the examples.

While the enhancement degree of the specific activity of MDH brought by the MDH activator of the present invention may vary depending on reaction conditions, concentration of the MDH activator and the like, it can usually increase the specific activity by 8 times or more under a suitable condition.

BEST MODE FOR CARRYING OUT THE INVENTION

Hereafter, the present invention will be further explained specifically with reference to the following examples.

<1> Searching for Gene Encoding Protein Exhibiting Amino Acid Sequence Homology with Alcohol Dehydrogenase Activator of Methanol Assimilating Bacillus As for the structure of the methanol dehydrogenase activator of Bacillus methanolicus strain C1, amino acid sequence of a small portion, i.e., that of 36 amino acids from the N-terminus, has already been known (The Journal of Biological Chemistry, 266, 3955–3960, 1991). Moreover, entire nucleotide sequences of some microorganism genomes have recently been determined and published. Therefore, amino acid sequence homology searching was performed based on the aforementioned amino acid sequence for a protein database, SWISS-PROT (European Bioinformatics Institute (EBI)), Release 34.0 by using Genetyx-Mac system (Software Development Co., Ltd.). As a result, the yqkg gene of Bacillus subtilis, of which function was unknown, was retrieved with high homology score. Therefore, it was decided to forcibly express this yqkG gene utilizing Escherichia Coli as a host to confirm if the yqkG actually coded for a protein functioning as an alcohol dehydrogenase activator.

<2> Cloning of Bacillus subtilis yqkg and Forced Expression thereof in Escherichia coli A region containing the open reading frame (ORF) of yqkG was amplified by PCR based on the already reported genomic nucleotide sequence information of the Bacillus subtilis strain 168. The DNA primers used were BsYqk-G1

(SEQ ID NO: 5 in Sequence Listing), and BsYqk-G2 (SEQ ID NO: 6 in Sequence Listing). BsYqk-G1 was incorporated with a recognition sequence for restriction enzyme ClaI in its 5' sequence. BsYqk-G2 was incorporated with a recognition sequence for restriction enzyme BamHI in its 5' sequence.

On the other hand, the genome was prepared from *Bacillus subtilis* 168 in a conventional manner (*Biochim. Biophy.* Acta, 72, 619–629 (1963)). The PCR reaction consisted of heat treatment at 94° C. for 90 seconds, 28 cycles of 98° C. for 10 seconds, 58° C. for 20 seconds, and 70° C. for 1 minute, and maintenance at 73° C. for 3 minutes, and was performed by using LA-Taq (produced by Takara Shuzo Co., Ltd.). A DNA fragment of a desired size was obtained by this reaction. This DNA fragment was purified, and treated with restriction enzymes ClaI and BamHI to obtain yqkG fragment having ClaI and BamHI digestion ends at its both ends.

On the other hand, plasmid pT13sNco (described in *J. Biochem.*, 104, 30–34 (1988)) having a tryptophan promoter (Ptrp) was used as a high expression plasmid for expression of the aforementioned DNA fragment. pT13sNco was digested with restriction enzymes ClaI and BamHI to obtain a vector portion as a larger fragment. This fragment was ligated to the above yqkG using T4-ligase to construct a yqkG expression plasmid pT-Bsb-yqkG1.

*Escherichia coli* JM109 was transformed with the plasmid pT-Bsb-yqkG1 in a conventional manner to obtain a transformant JM109/pT-Bsb-yqkG1. This transformant JM109/pT-Bsb-yqkG1 was given with a private number AJ13484, and it was deposited at the National Institute of Bioscience and Human-Technology, Agency of Industrial Science and Technology, Ministry of International Trade and Industry (postal code 305-8566, 1–3 Higashi 1-chome, Tsukuba-shi, Ibaraki-ken, Japan) on Aug. 12, 1998, and received an accession number of FERM P-16938, and transferred from the original deposit to the international deposit based on Budapest Treaty on Jun. 30, 1999, and has been deposited as an accession number of FERM BP-6774. As a control, *Escherichia coli* JM109 strain retaining the vector segment of pT13sNco, pTTNco, (JM109/pTTNco) was used.

These transformants were cultured in an M9-casamino acid-glucose medium (M9-CA-Glc medium) containing 100 mg/L of antibiotic ampicillin at 37° C., indoleacrylic acid (IAA), which is an inducer of transcription from Ptrp, was added to the medium to a final concentration of 25 μg/ml after about 2 hours, the culture was continued for further 6 hours, and then the cells were harvested from 4 ml of the medium. To these cells, 1 ml of suspension buffer (50 mM potassium phosphate (pH 7.6), 3 mM magnesium chloride, 1 mM dithiothreitol) was added, and the cells were suspended in it. Then, the cells were disrupted by ultrasonication, and centrifuged (15000 rpm, 30 minutes) to obtain a soluble fraction, which was used as a test sample.

<3> Cloning of *Bacillus brevis* mdh and Forced Expression of mdh in *Escherichia coli*

In order to verify MDH activity promoting activity of the aforementioned test sample, methanol dehydrogenase was prepared as follows.

From *Bacillus brevis* S1 strain (NCIMB No. 12524, obtained from NCIMB), which is a heat-tolerant methanol assimilating Bacillus, chromosome DNA was prepared in a conventional manner. The MDH gene was cloned by PCR using this DNA as template.

The DNA primers used were MDH-BM-1 (SEQ ID NO: 3 in Sequence Listing), and MDH-BM-2 (SEQ ID NO: 4 in Sequence Listing). These were produced by referring to the known nucleotide sequence of MDH gene of *Bacillus methanolicus* C1 (registered at GenBank with an entry name of BACMDH). The PCR reaction consisted of heat treatment at 94° C. for 90 seconds, 30 cycles of 98° C. for 10 seconds, 55° C. for 30 seconds, and 70° C. for 4 minutes, and maintenance at 72° C. for 10 minutes, and was performed by using LA-Taq (produced by Takara Shuzo Co., Ltd.). A DNA fragment of a desired size was obtained by this reaction. This DNA fragment was purified, and cloned into a commercially available vector pCR2.1 to obtain pCP-mdh24-1. Further, this was introduced into *Escherichia coli* JM109 strain to construct a transformant pCR-mdh24-1/JM109.

The transformant pCR-mdh24-1/JM109 was cultured overnight in 25 ml of LB medium containing 100 mg/L of antibiotic ampicillin at 37° C. with shaking. Then, the cells were collected by centrifugation in the same manner as in the aforementioned preparation of the yqkG gene. To these cells, buffer was added, and the cells were suspended in it. Then, the cells were disrupted by ultrasonication, and centrifuged again to prepare a soluble fraction containing methanol dehydrogenase.

MDH activity of the aforementioned MDH enzyme preparation was measured. The MDH activity was determined by estimating reduction of $NAD^+$ (nicotinamide adenine dinucleotide) accompanying the oxidation of methanol into formaldehyde through measurement of absorbance for light at a wavelength of 340 nm.

Specifically, a reaction solution [50 mM glycine/potassium hydroxide buffer (pH 9.5), 2 mM magnesium sulfate, 0.1 mM dithiothreitol, and 1 mM $NAD^+$] was put into cuvettes for spectrophotometer in an amount of 0.9 ml for each (for target sample and control), and maintained at 50° C. for 5 minutes. Then, 0.05 ml of the soluble cell fraction was added to the cuvette for the sample, and mixed, and the increase of absorbance was measured to confirm the background of the reaction. Then, the reaction was started by adding 0.1 ml of water into the cuvette for the control, or 0.05 ml of 12 M methanol into the cuvette for the sample, and methanol dehydrogenase activity was measured using the increase of absorbance for light at a wavelength of 340 nm accompanying the reduction of $NAD^+$ as an index.

As a result, when the cell extract obtained from the transformant pCR-mdh24-1/JM109 was used, significant methanol dehydrogenase activity was detected compared with the case of the control strains JM109/pTTNco.

<4> MDH Enzyme Activity Promoting Effect by YqKG

Then, it was confirmed if the soluble enzyme fraction of the transformant JM109/pT-Bsb-yqkG1 prepared as described in the aforementioned <2> could promote the enzyme activity of MDH.

0.04 ml of the soluble fraction of JM109/pTTNco (control), or the soluble fraction of JM109/pT-Bsb-yqkG1 (objective sample), and 0.04 ml of the soluble fraction of pCR-mdh24-1/JM109 (MDH enzyme sample) were mixed in advance. 0.08 ml of each mixture was added to 0.9 ml of reaction mixture [50 mM glycine/potassium hydroxide buffer (pH 9.5), 2 mM magnesium sulfate, 0.1 mM dithiothreitol, and 1 mM $NAD^+$] contained in a cuvette for activity measurement to measure the methanol dehydrogenase activity.

As a result, it was found that the soluble fraction of JM109/pT-Bsb-yqkG1 contained the activity that could promote MDH activity more than twice compared with the soluble fraction of JM109/pTTNco (Table 1).

TABLE 1

Promotion of enzyme reaction by alcohol dehydrogenase activator

| Added sample[1] | Δ OD 340 nm/min | Activation ratio[2] (%) |
|---|---|---|
| JM109/pT-Bsb-yqkG | 0.792 | 250 |
| JM109/PTTNco (Control) | 0.318 | 100 |

[1] Sample added to crude enzyme fraction containing alcohol dehydrogenase
[2] Value calculated based on alcohol dehydrogenase activity in control sample defined 100%

<5> Explanation of Sequence Listing

SEQ ID NO: 1; amino acid sequence of the activator YqkG,

SEQ ID NO: 2; nucleotide sequence of the coding region for yqkG 3,

SEQ ID NO: 3; upstream primer MDH-BM-1 for PCR cloning of MDH,

SEQ ID NO: 4; downstream primer MDH-BM-2 for PCR cloning of MDH,

SEQ ID NO: 5; upstream primer BS-YQKG1—1 for PCR cloning of yqkG,

SEQ ID NO: 6; downstream primer BS-YqkG2—2 for PCR cloning of yqkG,

SEQ ID NO: 7; amino terminal sequence of MDH activator of *Bacillus methanolicus* C1.

What is claimed is:

1. A method for producing a methanol dehydrogenase activator, comprising
culturing a cell containing an isolated polynucleotide encoding the methanol dehydrogenase activator having the amino acid sequence of SEQ ID NO:2 in a medium suitable for producing the methanol dehydrogenase activator; and collecting the methanol dehydrogenase activator.

2. A method for enhancing the activity of a methanol dehydrogenase in a cell, comprising culturing a cell containing an isolated polynucleotide encoding the methanol dehydrogenase activator having the amino acid sequence of SEQ ID NO:2 in a medium suitable for producing the methanol dehydrogenase activator, wherein said methanol dehydrogenase activator enhances the activity of the methanol dehydrogenase in said cell.

3. A method for enhancing the activity of a methanol dehydrogenase in a cell, comprising culturing a cell containing an isolated polynucleotide which hybridizes under stringent conditions to SEQ ID NO:1 and which codes the methanol dehydrogenase activator, wherein the stringent conditions are washing at 60° C. in 1×SSC and 0.1% SDS; wherein said methanol dehydrogenase activator enhances the activity of the methanol dehydrogenase in said cell.

* * * * *

SEQUENCE LISTING

```
<160> NUMBER OF SEQ ID NOS: 7

<210> SEQ ID NO 1
<211> LENGTH: 555
<212> TYPE: DNA
<213> ORGANISM: Bacillus subtilis
<220> FEATURE:
<221> NAME/KEY: CDS
<222> LOCATION: (1)..(555)

<400> SEQUENCE: 1 atg aaa tca tta gaa gaa gaa aca att gcc aaa gaa cag att ttt tcg      48
Met Lys Ser Leu Glu Glu Glu Thr Ile Ala Lys Glu Gln Ile Phe Ser
 1               5                  10                  15 ggt aaa gtc att gat ctt tat gtc gag gat gta gag ctg cca aac ggc      96
Gly Lys Val Ile Asp Leu Tyr Val Glu Asp Val Glu Leu Pro Asn Gly
            20                  25                  30 aaa gcc agt aaa cgt gaa att gtg aaa cac cct gga gct gta gcg gta     144
Lys Ala Ser Lys Arg Glu Ile Val Lys His Pro Gly Ala Val Ala Val
        35                  40                  45 cta gcc gtc aca gat gaa ggg aaa atc atc atg gtc aaa caa ttc cgt     192
Leu Ala Val Thr Asp Glu Gly Lys Ile Ile Met Val Lys Gln Phe Arg
    50                  55                  60 aag ccg ctt gag cgg acg atc gtt gaa att ccg gcc ggt aag ctt gaa     240
Lys Pro Leu Glu Arg Thr Ile Val Glu Ile Pro Ala Gly Lys Leu Glu
65                  70                  75                  80 aaa ggt gag gag ccg gag tat acg gca ctt cgg gaa ctt gaa gag gaa     288
Lys Gly Glu Glu Pro Glu Tyr Thr Ala Leu Arg Glu Leu Glu Glu Glu
                85                  90                  95 acc ggt tat aca gca aaa aaa ctg aca aaa ata act gcg ttt tat aca     336
Thr Gly Tyr Thr Ala Lys Lys Leu Thr Lys Ile Thr Ala Phe Tyr Thr
            100                 105                 110 tca ccc gga ttt gca gat gaa atc gtt cac gtt ttt ctt gct gag gag     384
Ser Pro Gly Phe Ala Asp Glu Ile Val His Val Phe Leu Ala Glu Glu
        115                 120                 125
```

```
ctt tct gtg ctt gaa gaa aaa cgg gag ctt gat gag gac gag ttt gtt      432
Leu Ser Val Leu Glu Glu Lys Arg Glu Leu Asp Glu Asp Glu Phe Val
        130                 135                 140 gaa gtg atg gag gtg acg ctt gaa gat gcg cta aag ctg gtt gaa tcg      480
Glu Val Met Glu Val Thr Leu Glu Asp Ala Leu Lys Leu Val Glu Ser
145                 150                 155                 160 cgt gaa gta tat gat gct aaa aca gcc tac gcg att cag tat ctt cag      528
Arg Glu Val Tyr Asp Ala Lys Thr Ala Tyr Ala Ile Gln Tyr Leu Gln
                165                 170                 175 ctg aaa gaa gcg ctc caa gca caa aaa                                  555
Leu Lys Glu Ala Leu Gln Ala Gln Lys
        180                 185

<210> SEQ ID NO 2
<211> LENGTH: 185
<212> TYPE: PRT
<213> ORGANISM: Bacillus subtilis

<400> SEQUENCE: 2

Met Lys Ser Leu Glu Glu Thr Ile Ala Lys Glu Gln Ile Phe Ser
 1               5                  10                  15

Gly Lys Val Ile Asp Leu Tyr Val Glu Asp Val Glu Leu Pro Asn Gly
                20                  25                  30

Lys Ala Ser Lys Arg Glu Ile Val Lys His Pro Gly Ala Val Ala Val
            35                  40                  45

Leu Ala Val Thr Asp Glu Gly Lys Ile Ile Met Val Lys Gln Phe Arg
    50                  55                  60

Lys Pro Leu Glu Arg Thr Ile Val Glu Ile Pro Ala Gly Lys Leu Glu
65                  70                  75                  80

Lys Gly Glu Glu Pro Glu Tyr Thr Ala Leu Arg Glu Leu Glu Glu Glu
                85                  90                  95

Thr Gly Tyr Thr Ala Lys Lys Leu Thr Lys Ile Thr Ala Phe Tyr Thr
                100                 105                 110

Ser Pro Gly Phe Ala Asp Glu Ile Val His Val Phe Leu Ala Glu Glu
            115                 120                 125

Leu Ser Val Leu Glu Glu Lys Arg Glu Leu Asp Glu Asp Glu Phe Val
        130                 135                 140

Glu Val Met Glu Val Thr Leu Glu Asp Ala Leu Lys Leu Val Glu Ser
145                 150                 155                 160

Arg Glu Val Tyr Asp Ala Lys Thr Ala Tyr Ala Ile Gln Tyr Leu Gln
                165                 170                 175

Leu Lys Glu Ala Leu Gln Ala Gln Lys
        180                 185

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:Primer
      MDH-BM-1

<400> SEQUENCE: 3 taaaaggat ccccgatgat acaacaccaa acgg                                 34

<210> SEQ ID NO 4
<211> LENGTH: 33
<212> TYPE: DNA
<213> ORGANISM: Artificial Sequence
```

```
<220> FEATURE:
<223> OTHER INFORMATION: Description of Artificial Sequence:MDH-BM-2

<400> SEQUENCE: 4
gaccgaattc catgtagttt ttcctcattc acc                          33

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence:BS-YQKG1-1

<400> SEQUENCE: 5
gggaatcgat aaatgaaat cattagaaga aaaacaatt gcc                 43

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence:BS-YQKG2-2

<400> SEQUENCE: 6
taaatggatc cttttcagcc gggctgacag ccagtttg                     38

<210> SEQ ID NO 7
<211> LENGTH: 36
<212> TYPE: PRT
<213> ORGANISM: Bacillus subtilis

<400> SEQUENCE: 7

Gly Lys Leu Phe Glu Glu Lys Thr Ile Lys Thr Glu Gln Ile Phe Ser
 1               5                  10                  15

Gly Arg Val Val Lys Leu Gln Val Asp Asp Arg Glu Tyr Pro Asn Gly
            20                  25                  30

Gln Thr Val Lys
         35
```